(12) United States Patent
Chen et al.

(10) Patent No.: US 10,632,160 B2
(45) Date of Patent: Apr. 28, 2020

(54) PROBIOTIC COMPOSITION FOR PREVENTING, IMPROVING OR ALLEVIATING PANCREATIC CANCER AND APPLICATION THEREOF

(71) Applicant: GenMont Biotech Incorporation, Tainan (TW)

(72) Inventors: Yi-Hsing Chen, Tainan (TW); Wan-Hua Tsai, Kaohsiung (TW); Wen-Ling Yeh, Tainan (TW); Ming-Shiou Jan, Taichung (TW); Yen-Wan Hsiao, Taichung (TW); Li-Jin Hsu, Tainan (TW); Junko Sugawara, Taichung (TW)

(73) Assignee: GENMONT BIOTECH INCORPORATION, Tainan (TW)

( * ) Notice: Subject to any disclaimer, the term of this patent is extended or adjusted under 35 U.S.C. 154(b) by 0 days.

(21) Appl. No.: 16/361,599

(22) Filed: Mar. 22, 2019

(65) Prior Publication Data
US 2019/0290707 A1 Sep. 26, 2019

(30) Foreign Application Priority Data
Mar. 23, 2018 (CN) .......................... 2018 1 0244949

(51) Int. Cl.
*A61K 35/747* (2015.01)
*A61P 35/00* (2006.01)
*C12R 1/225* (2006.01)
*A61K 35/00* (2006.01)

(52) U.S. Cl.
CPC ............ *A61K 35/747* (2013.01); *A61P 35/00* (2018.01); *C12R 1/225* (2013.01); *A61K 2035/115* (2013.01)

(58) Field of Classification Search
None
See application file for complete search history.

(56) References Cited

FOREIGN PATENT DOCUMENTS

| TW | I346554 B | 8/2011 |
|---|---|---|
| TW | I398259 B | 6/2013 |

OTHER PUBLICATIONS

Peña, Jeremy A. et al., Probiotic Lactobacillus spp. Diminish Helicobacter hepaticus-Induced Inflammatory Bowel Disease in Interleukin-10-Deficient Mice, Infection and Immunity, Feb. 2005, p. 912-920, vol. 73, No. 2, American Society for Microbiology, US.
Jan, Ming-Shiou et al., Abstract 235: Probiotics ameliorate Porphyromonas gingivalis-promoted pancreatic cancer progression in oncogenic Kras transgenic mice, Jul. 2017, vol. 77, Issue 13, American Association for Cancer Research, Washington DC.

*Primary Examiner* — Padmavathi Baskar
(74) *Attorney, Agent, or Firm* — Fay Sharpe LLP

(57) ABSTRACT

The present invention relates to a probiotic composition for preventing, improving or alleviating pancreatic cancer and a method for preventing, improving or alleviating the pancreatic cancer and its complications using the probiotic composition. The probiotic composition, which is consisted of specific strains and specific ratio of *Lactobacillus paracasei* to *Lactobacillus reuteri*, can significantly improve or alleviate various symptomatic indicators and severity of pancreatic cancer, thereby being applied on a method for preventing, improving or alleviating the pancreatic cancer and its complications using an oral composition including the *Lactobacillus* strains.

6 Claims, 6 Drawing Sheets
(5 of 6 Drawing Sheet(s) Filed in Color)
Specification includes a Sequence Listing.

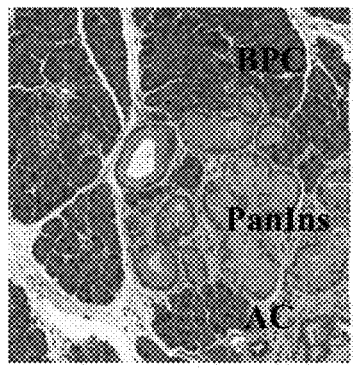 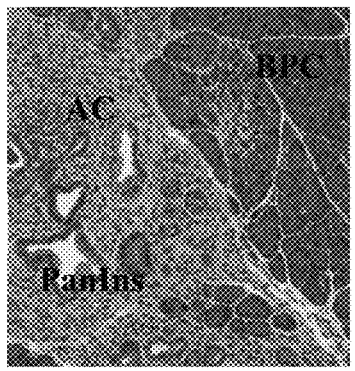 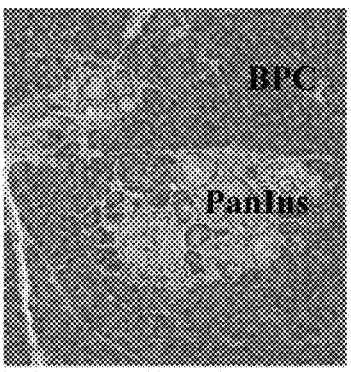
Fig. 2A  Fig. 2B  Fig. 2C
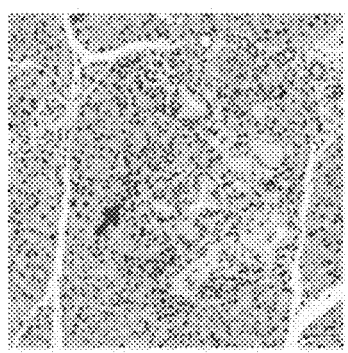 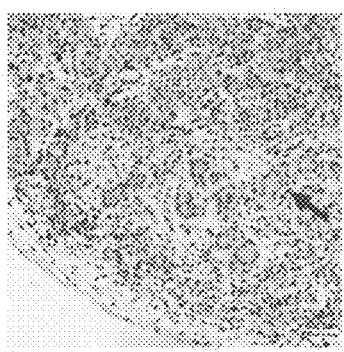 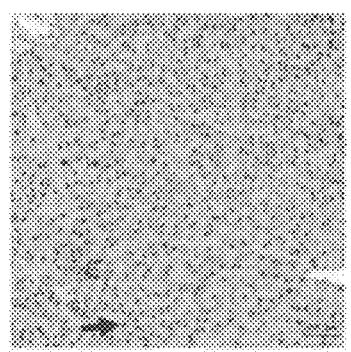
Fig. 3A  Fig. 3B  Fig. 3C

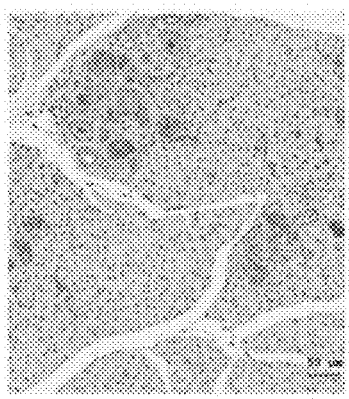 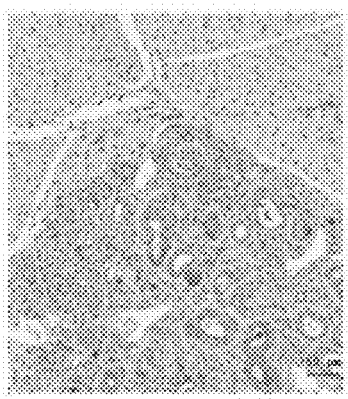 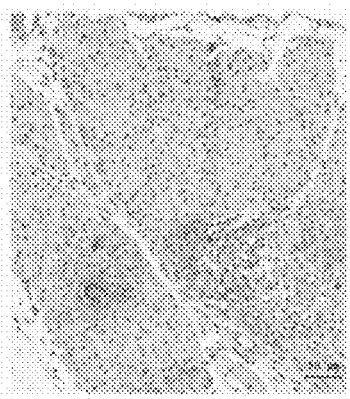
Fig. 6A					Fig. 6B					Fig. 6C
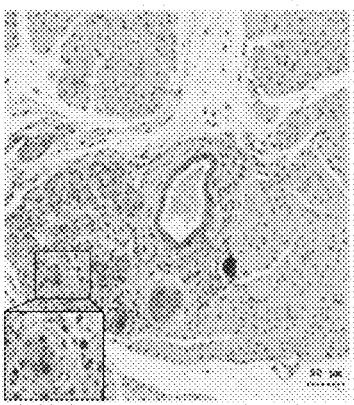  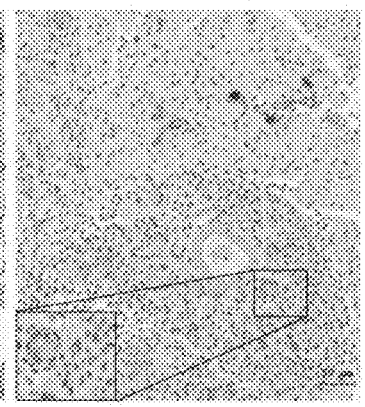
Fig. 6D					Fig. 6E					Fig. 6F

PROBIOTIC COMPOSITION FOR PREVENTING, IMPROVING OR ALLEVIATING PANCREATIC CANCER AND APPLICATION THEREOF

RELATED APPLICATIONS

This application claims benefit of priority from China Patent Application No. 201810244949.4, filed on Mar. 23, 2018, the entirety of which is incorporated by reference herein.

BACKGROUND

Field of Invention

A sequence listing is being submitted herein as an ASCII text file with the name "Sequence_Listing.txt", created on Mar. 21, 2019, with a file size of 2,245 bytes. The material in this text file is hereby fully incorporated by reference herein.

The present invention relates to a probiotic composition and an application thereof, and particularly to a probiotic composition for preventing, improving, or alleviating pancreatic cancer and an application thereof.

Description of Related Art

According to the data statistics from Ministry of Health and Welfare (MOHW) in Taiwan, the pancreatic cancer the eighth leading cause of cancer-related death in 2016. However, the pancreatic cancer has been one of the most lethal cancers because it is hardly diagnosed in early stages. Unfortunately, after diagnosis of the pancreatic cancer, up to 52% of patients with the stage IV has only a few months of survival duration from the time of diagnosis until demis, with few of them being able to get well controlled through surgery. Currently, chemotherapy is the most common treatment for the pancreatic cancer; however, its therapeutic effect and the five-year survival rate are not satisfactory. Therefore, it is necessary to develop a better strategy to prevent and treat pancreatic cancer.

In the past, it is believed that the pancreatic cancer can occur due to the following dangerous factors: heavy drinking, diabetes, smoking, acute and chronic pancreatitis, blood types, genetic inheritance and so on. According to the statistical results from epidemiological research in recent years, it is found that the pancreatic cancer positively correlates with the incidence of periodontosis. Moreover, the antibody against the pathogen of the periodontosis, *Porphyromonas gingivalis* (*P. gingivalis*), is also detected within blood specimens of patients diagnosed with pancreatic cancer, supposing that the severity of pancreatic cancer may correlate with the pathogen.

More and more reports indicate that cancer has been found correlated to the gut microbiota. It is possible to prevent and treat various cancers via administration of specific probiotics. For example, some probiotics can kill cancer cells directly. Some probiotics can enhance immunity of a host or achieving the effect of assisting an immunosuppressor. In addition, some probiotics are helpful to prevent and treat the colorectal cancer. However, there are few evidence-based researches (EBR) on prevention and treatment of pancreatic cancer associated with probiotics.

In view of the above, it is necessary to provide a probiotic composition so as to prevent, improve or alleviate the symptoms and severity of pancreatic cancer.

SUMMARY

Therefore, one aspect of the present invention provides a probiotic composition for preventing, improving or alleviating the pancreatic cancer, including *Lactobacillus paracasei* and *Lactobacillus reuteri*.

Another aspect of the present invention provides a method for preventing, improving or alleviating the pancreatic cancer and its complications using a probiotic composition, which is to administrate the aforementioned probiotic composition to an subject orally at an effective dose per day for a given period so as to reduce the symptomatic indicator and/or indicator protein of the pancreatic cancer of the subject.

According to the aforementioned aspects, a probiotic composition for preventing, improving or alleviating pancreatic cancer is provided, which includes *Lactobacillus paracasei* GMNL-133 and *Lactobacillus reuteri* GMNL-89, in which the ratio of the *Lactobacillus paracasei* GMNL-133 to the *Lactobacillus reuteri* GMNL-89 in the bacterial cells can be 2:1 to 1:2, for example.

In the aforementioned embodiments, *Lactobacillus paracasei* GMNL-133 can be, for example, a strain deposited with an accession number of CCTCC M 2011331 in China Center for Type Culture Collection (CCTCC), Wuhan University, Wuhan 430072, People's Republic of China, on Sep. 26, 2011. *Lactobacillus paracasei* GMNL-133 is also deposited with an accession number of BCRC 910520 in Bioresource Collection and Research Center (BCRC) of Food Industry Research and Development Institute (FIRDI) at No. 331 on Shih-Pin Road, Hsinchu, Taiwan, on Jul. 5 2011. The aforementioned *Lactobacillus reuteri* GMNL-89 can be, for example, a strain deposited with an accession number of CCTCC M 207154 in China Center for Type Culture Collection (CCTCC), Wuhan University, Wuhan 430072, People's Republic of China, on Nov. 19, 2007. *Lactobacillus reuteri* GMNL-89 is also deposited with an accession number of BCRC 910340 in BCRC of FIRDI at No. 331 on Shih-Pin Road, Hsinchu, Taiwan, on Nov. 14, 2006.

In an embodiment of the present invention, the aforementioned ratio of the *Lactobacillus paracasei* GMNL-133 to the *Lactobacillus reuteri* GMNL-89 in the bacterial cells can be 1:1, for example.

According to another aspect of the present invention, a method for preventing, improving or alleviating the pancreatic cancer and its complications using the probiotic composition is provided, which includes orally administrating the aforementioned probiotic composition to an subject at an effective dose per day of $8.2 \times 10^8$ colony forming units (CFUs) per kg of body weight for 4 weeks, so as to reduce the symptomatic indicator and/or indicator protein of the subject.

In an embodiment of the present invention, the aforementioned composition is an oral composition.

By applying the probiotic composition of the present invention for preventing, improving or alleviating the pancreatic cancer, the specific strains of *Lactobacillus paracasei* and *Lactobacillus reuteri* included in the probiotic composition can significantly improve various symptomatic indicators and severity of the pancreatic cancer, and the composition is further applied in the oral composition for preventing, improving, or alleviating the pancreatic cancer.

BRIEF DESCRIPTION OF THE DRAWINGS

The patent or application file contains at least one drawing executed in color. Copies of this patent or patent application publication with color drawing(s) will be provided by Office upon request and payment of the necessary fee. The disclosure can be more fully understood by reading the following detailed description of the embodiment, with reference made to the accompanying drawings as follows.

FIGS. 2A to 2C show an immunohistostaining section diagram of pancreas of a mouse suffering from pancreatic cancer after the administration of the probiotic composition in accordance with one embodiment of the present invention.

FIGS. 3A to 3C show an immunohistostaining section diagram of proliferating cell nuclear antigen (PCNA) of a pancreas of a mouse suffering from pancreatic cancer after the administration of the probiotic composition in accordance with one embodiment of the present invention.

FIGS. 6A to 6F show an immunohistostaining section diagram of TGF-β (FIGS. 6A to 6C) and activated (phosphorylated) Smad3 (FIGS. 6D to 6F) protein of pancreas of a mouse suffering from pancreatic cancer after the administration of the probiotic composition in accordance with one embodiment of the present invention.

DETAILED DESCRIPTION

Figure 1:
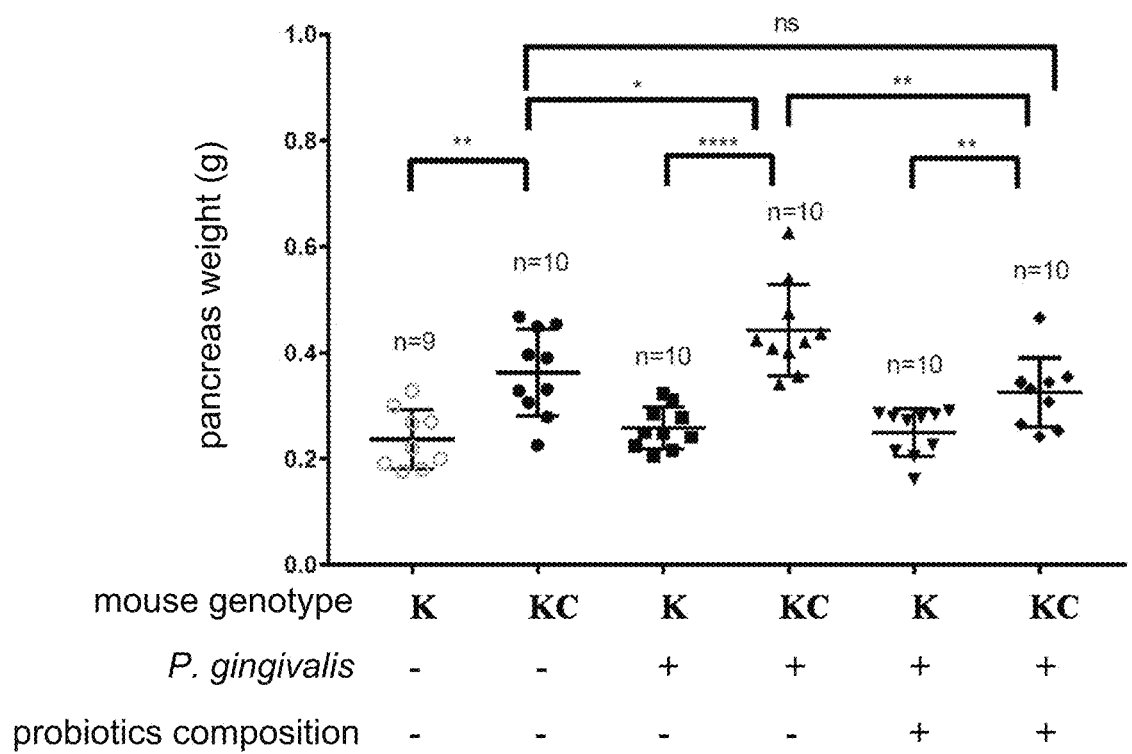
FIG. 1 shows a diagram of pancreas weight distribution of a mouse suffering from pancreatic cancer after administration of the probiotic composition in accordance with one embodiment of the present invention.

Singular forms, "a", "an", and "the", as mentioned in the present invention also cover plural references, unless otherwise stated in the context. A value range (such as 10% to 11% of A) includes its upper and lower limits (i.e. 10%≤A≤11%) if not otherwise stated specially; the value range, for which if no lower limit is defined (such as B lower than 0.2%, or B below 0.2%), can have a lower limit of zero (i.e. 0%≤B≤0.2%). The aforementioned terms are used for illustrating and helping understand the present invention rather than limiting the scope thereof.

The present invention provides a probiotic composition for preventing, improving or alleviating pancreatic cancer, which includes specific strains of *Lactobacillus paracasei* and *Lactobacillus reuteri* and can significantly prevent, improve, or alleviate various symptomatic indicators and severity of the pancreatic cancer.

In one embodiment, the aforementioned specific strains of *Lactobacillus paracasei* and *Lactobacillus reuteri* refer to the *Lactobacillus paracasei* GMNL-133 and the *Lactobacillus reuteri* GMNL-89. In particular, the aforementioned *Lactobacillus paracasei* GMNL-133 refers to a strain deposited with an accession number of CCTCC M 2011331 in China Center for Type Culture Collection (CCTCC), Wuhan University, Wuhan 430072, People's Republic of China, on Sep. 26, 2011. *Lactobacillus paracasei* GMNL-133 is also deposited with an accession number of BCRC 910520 in Bioresource Collection and Research Center (BCRC) of Food Industry Research and Development Institute (FIRDI) at No. 331 on Shih-Pin Road, Hsinchu, Taiwan, on Jul. 5, 2011. The aforementioned *Lactobacillus reuteri* GMNL-89 refers to a strain deposited with an accession number of CCTCC M 207154 in China Center for Type Culture Collection (CCTCC), Wuhan University, Wuhan 430072, People's Republic of China, on Nov. 19, 2007. *Lactobacillus reuteri* GMNL-89 is also deposited with an accession number of BCRC 910340 in BCRC of FIRDI at No. 331 on Shih-Pin Road, Hsinchu, Taiwan, on Nov. 14, 2006.

In the aforementioned embodiments, a ratio of the *Lactobacillus paracasei* GMNL-133 to the *Lactobacillus reuteri* GMNL-89 in bacterial cells can be 2:1 to 1:2, for example. In one example, the ratio of the *Lactobacillus paracasei* GMNL-133 to the *Lactobacillus reuteri* GMNL-89 in the bacterial cells can be 1:1, for example.

In an embodiment of the present invention, the aforementioned probiotic composition can effectively prevent, improve, or alleviate the symptomatic indicator and the severity of the pancreatic cancer.

The symptomatic indicator referred to herein in the present invention can include but be not limited to inhibiting the swelling of pancreas, mitigating the tumorigenesis (such as pancreatic intraepithelial neoplasia and adenocarcinoma) in a mouse with pancreatic cancer, inhibiting the proliferation of the pancreas cells, reducing the fibrosis of the pancreas (such as reducing the expression level of collagen) and inhibiting the expression level of cancer metastasis indicator protein (such as N-Cad, Vimentin, Snail-1 and ZEB).

The severity referred to herein in the present invention can include but be not limited to improve or alleviating the pancreatic cancer severity by modulating the immunity path (for example, promoting the expression level of TGF-β and activating the expression level of its downstream protein, activated (phosphorylated) Smad3).

In an embodiment, the aforementioned probiotic composition can further be used for manufacturing a composition for preventing, improving, or alleviating the pancreatic cancer and/or its complications. In the aforementioned embodiments, the aforementioned composition is an oral composition. In an example, the aforementioned complication can include but be not limited to pancreas intraepithelial neoplasia, adenocarcinoma, pancreas fibrosis, and immunity diseases related to the pancreatic cancer.

In an embodiment of the present invention, the aforementioned composition can include but be not limited to the aforementioned ratio of the *Lactobacillus paracasei* GMNL-133 to the *Lactobacillus reuteri* GMNL-89 in the bacterial cells, a pharmaceutically acceptable carrier can be optionally added therein. When the pharmaceutical composition is a composition for internal use, the carrier can be a water-dominant carrier, such as a physiological buffer, and the pharmaceutical composition is orally administrated.

In an embodiment of the present invention, when the aforementioned probiotic composition is used for manufacturing a composition for preventing, improving, or alleviating the pancreatic cancer and its complications, there is no particular limitation on the cell concentration of the aforementioned probiotic composition, and the cell concentration is adjusted depending on the subject's weight, and the composition is administrated at an effective dose per day of $8.2 \times 10^8$ colony forming units (CFUs) per kg of body weight, for example. In an example of a mouse (with an average weight of 20 g, for example), a total count of bacteria in the probiotic composition can be preferably $0.5 \times 10^7$ CFU to $3.0 \times 10^7$ CFU for a mouse, and more preferably $1.64 \times 10^7$ CFU for a mouse, rather than limiting the scope thereof.

The application of the present invention is illustrated by using following embodiments, but these embodiments should not be considered as limiting the present invention. Various modification and changes can be made by one of ordinary skills in the art to which the present invention pertains, without departing from the spirit and scope of the present invention.

Example 1. Bacteriological Feature Assessment of *Lactobacillus paracasei* GMNL-133 and *Lactobacillus reuteri* GMNL-89

Examples hereinafter provide the assessments of bacteriological characteristics of the *Lactobacillus paracasei* GMNL-133 and *Lactobacillus reuteri* GMNL-89.

1. The Bacteriological Feature of *Lactobacillus paracasei* GMNL-133

*Lactobacillus paracasei* GMNL-133 was originally isolated from human small intestinal tracts.

*Lactobacillus paracasei* GMNL-133 had the following appearance characteristics. *Lactobacillus paracasei* GMNL-133 was inoculated on the MRS (De Man, Rogosa and Sharpe) agar culture plate and incubated under 37° C. for 48 hours, and then observed for its morphology. The appearance, size, and color of the colony: it had an intact edge, an average size of 2.5 mm×2.5 mm, a milky white color, and a smooth and swelling surface. Its Gram staining showed positive. Its morphology was rod-shaped (*bacillus*). It had no spore formation. It had no mobility.

*Lactobacillus paracasei* GMNL-133 had the following physiological characteristics. *Lactobacillus paracasei* GMNL-133 was grown under a facultative anaerobic condition of 35° C. to 40° C. and pH 4.0 to 7.0.

In addition, after extracting the total RNA of *Lactobacillus paracasei* GMNL-133 by conventional methods, a partial sequence of 16S rRNA gene was amplified by a pair of primers as shown in SEQ ID NOs: 1 and 2 (the forward primer was PAF primer, and the reverse primer was 536R primer), in which a resultant nucleic acid fragment was as shown in SEQ ID NO: 3. The method of extracting the total RNA was well known to one of ordinary skills in the art of the present invention rather than repeatedly reciting in detail.

This nucleic acid fragment had a sequence identity of 100% to two 16S rRNA gene sequences of *Lactobacillus paracasei* (GenBank Nos.: NR 041054.1, NR_025880.1) in the GenBank of the U.S.A. National Center for Biotechnology Information (NCBI) during alignment. In addition, SEQ ID NO:3 also had a sequence identity of 99% to the other two 16S rRNA gene sequences of *Lactobacillus paracasei* (GenBank Nos.: NR_113337.1, NR_117987.1) during alignment, such that SEQ ID NO:3 was confirmed as *Lactobacillus paracasei*.

2. The Bacteriological Feature of *Lactobacillus reuteri* GMNL-89

*Lactobacillus reuteri* GMNL-89 was originally isolated from human small intestinal tracts.

*Lactobacillus reuteri* GMNL-89 had the following appearance characteristics. *Lactobacillus reuteri* GMNL-89 was inoculated on the MRS agar culture plate and incubated under 37° C. for 48 hours, and then observed for its morphology. The appearance, size, and color of the colony: it had intact edge, an average size of 2.5 mm×2.5 mm, a milky white color, and a smooth and swelling surface. Its Gram staining showed positive. Its morphology was rod-shaped (*bacillus*). It had no spore formation. It had no mobility.

*Lactobacillus reuteri* GMNL-89 had the following physiological characteristics. *Lactobacillus reuteri* GMNL-89 was grown under a facultative anaerobic condition of 35° C. to 40° C. and pH 4.0 to 7.0.

In addition, after extracting the total RNA of *Lactobacillus reuteri* GMNL-89 by conventional methods, a partial sequence of 16S rRNA gene was amplified by a pair of primers as shown in SEQ ID NOs: 1 and 2 (the forward primer was PAF primer, and the reverse primer was 536R primer), in which a resultant nucleic acid fragment was as shown in the SEQ ID NO: 4. The method of extracting the total RNA was well known to one of ordinary skills in the art of the present invention rather than repeatedly reciting in detail.

This nucleic acid fragment has a sequence identity of 99% to two 16S rRNA gene sequences of *Lactobacillus paracasei* (GenBank Nos.: NR_075036.1, NR_113820.1, and NR_119069.1, in which NR_075036.1 and NR_119069.1 were of the same strain) after alignment, such that SEQ ID NO: 4 was confirmed as *Lactobacillus reuteri*.

Example 2. Establishment of Animal Model for Mouse with Pancreatic Cancer

This Example used LSL-Kras$^{G12D}$ transgenic mice (hereinafter referred to as the K genotype mice) and LSL-Kras$^{G12D}$; Pdx-1-Cre transgenic mice (hereinafter referred to as the KC-genotype mice) to assess the effect of the probiotic composition in preventing, improving or alleviating the symptomatic indicator of the pancreatic cancer, as well as modulating TGF-β-related signaling pathways.

The aforementioned K genotype mice and the KC-genotype mice (half male and half female) were commercially available from the Mutant Mouse Resource & Research Centers [MMRRC; website: https://www.mmrrc.org/; formerly known as the National Cancer Institute (NCI) Mouse Repository], under the strain of B6.129-Kras$^{tm4Tyj}$ (i.e. those having LSL-Kras$^{G12D}$ gene; K genotype mice) and B6.FVB-Tg (Ipf1-cre)1Tuv (i.e. those having Pdx-1-Cre gene; C genotype mice). After carrying out the gene background purification on them into a B6 genotype background, these two genotype mice were put into hybridization to implement the genotype identification in a PCR way, so as to select the transgenic mice carrying the LSL-Kras$^{G12D}$ (K genotype mice) and the double transgenic mice carrying LSL-Kras$^{G12D}$ and Pdx-1-Cre (i.e. carrying double genes that were LSL-Kras$^{G12D}$ and Pdx-1-Cre genes; KC-genotype mice) for experiments in accordance with the guidelines for Institutional Animal Care and Use Committee (IACUC), established by the Committees of National Cheng Kung University and the Chung Shan Medical University, as well as related regulations of Taiwan Animal Protection Law.

In brief, whether the transgene was expressed in the aforementioned transgenic mice was under control of the Cre gene. The K genotype mice carried the LSL-Kras$^{G12D}$ gene, but the Kras$^{G12D}$ would not be expressed greatly due to lack of expressed Cre gene, and such mice could be assigned to a control group without pancreatic cancer in a control group.

A KC-genotype mouse cell carried the LSL-Kras$^{G12D}$; Pdx-1-Cre gene, could greatly express Kras$^{G12D}$ protein in the pancreas cell, and could spontaneously produce pancreatic cancer in an aged KC-genotype mouse. After the *Porphyromonas gingivalis* was applied to a KC-genotype mouse in its oral cavity, it could accelerate and induce the severity of pancreatic cancer, so such mouse was assigned to in the test group (or referred to as the treatment group) with pancreatic cancer.

Before the experiment, the aforementioned mice firstly drink the antibiotic-containing water randomly for 10 days, and the water was changed per 5 days. On the eleventh day, the water was replaced with re-osmosis (R.O.) water for 3 days to excrete residual antibiotics in those mice. *P. gingivalis* was applied to mice of the treatment group in their gingiva and oral mucosa ($1\times10^9$ CFUs/mouse) once per 2 days, three times in total, so as to accelerate inducing the occurrence of pancreatic cancer. Next, the mice were orally fed (i.e., tube feeding) a probiotic composition consisting of *Lactobacillus paracasei* GMNL-133 and *Lactobacillus reuteri* GMNL-89 (in which a total count of bacteria was $1.64\times10^7$ CFUs/mouse, or $8.2\times10^8$ CFUs/per kg of weight, and the two strains were mixed at a ratio of 1:1 in the bacterial cells). After 4 weeks, the mice were sacrificed.

After the mouse pancreas were weighed, the pancreas tissue was fixed, embedded, and sliced in order to do Hematoxylin & Eosin staining, Masson's trichrome staining (mainly observing the collagen), and immunohistostaining of specific proteins [such as the proliferating cell nuclear antigen (PCNA), N-cadherin (N-Cad), vimentin, the transcription factor Snail-1, zinc finger E-box binding homeobox (ZEB) protein, TGF-β, phosphorylated Smad3 (phospho-Smad3) protein], experimental data of which will be determined by experts.

Example 3. Assessment of Effect of Symptomatic Indicator of Probiotic Composition for Preventing, Improving or Alleviating Pancreatic Cancer 1. Assessment of Inhibiting Effect of Probiotic Composition on Pancreas Swelling Referring to FIG. 1, it showed a pancreas weight distribution diagram of a mouse with pancreatic cancer after the oral administration of a probiotic composition according to one embodiment of the present invention. In FIG. 1, the vertical axis represented the pancreas weight (g), and the horizontal axis represented each treatment group, in which the symbol + represented this treatment done, the symbol − represented this treatment not done, the symbol ○ represented the pancreas weight of an untreated K genotype mouse, the symbol ● represented the pancreas weight of an untreated KC-genotype mouse, the symbol ■ represented the pancreas weight of a K genotype mouse treated with *P. gingivalis*, the symbol ▲ represented the pancreas weight of a KC-genotype mouse treated with *P. gingivalis*, the symbol ▼ represented the pancreas weight of a K genotype mouse treated with *P. gingivalis* and administrated with the probiotic composition, and the symbol ♦ represented the pancreas weight of a KC-genotype mouse treated with *P. gingivalis* and administrated with the probiotic composition, the symbol "*" represented the two groups of average values±standard deviation had a statistically significant difference (P<0.05) therebetween, the symbol "" represented the two groups of average values±standard deviation had a statistically significant difference (P<0.01) therebetween, the symbol "**" represented the two groups of average values±standard deviation had a statistically significant difference (P<0.0001) therebetween, ns (no significance) represented the two groups of average values±standard deviation had no statistically significant difference (P>0.05) therebetween, and n represented the sample number of the group.

It was shown by the result of the symbols ○ and ● in FIG. 1 that, the pancreas weight of the untreated KC-genotype mouse was increased to an extent greater than the pancreas weight of the untreated K genotype mouse, indicating that the great expression level of $Kras^{G12D}$ would increase the pancreas weight.

Next, it was shown by the result of symbols ● and ▲ in FIG. 1, after the KC-genotype mice were applied with *P. gingivalis* in the oral cavities to induce the pancreatic cancer, the pancreas weight increased or the swelling became significant, indicating that *P. gingivalis* indeed could aggravate the pancreatic cancer severity.

However, it was shown by the result of the symbols ▲ and ♦ in FIG. 1 that the oral probiotic composition could reduce the pancreas weight or swelling caused by applying the KC-genotype mice with *P. gingivalis*, even with an average value slightly less than the value range of the untreated group (results of symbols ● and ♦). Although it was not statistically significant in pancreas weight (for example, there was no statistically significant difference, ns, as shown in the results between the symbols ● and ♦), it was proven that the probiotic composition consisted of *Lactobacillus paracasei* GMNL-133 and *Lactobacillus reuteri* GMNL-89 could indeed inhibit the mouse pancreas weight increment or swelling.

2. Assessment of Effect of Probiotic Composition Improving or Mitigating Neoplasia of Mouse with Pancreatic Cancer Referring to FIGS. 2A to 2C, they showed immunohistostaining section diagrams of pancreas of the mice suffering from pancreatic cancer after the administration of the probiotic composition in accordance with one embodiment of the present invention, in which FIG. 2A represented an immunohistostaining section diagram of pancreas of the untreated KC-genotype mice, FIG. 2B represented a immunohistostaining section diagram of pancreas of the KC-genotype mice with *P. gingivalis* applied in their oral cavities, FIG. 2C represented an immunohistostaining section diagram of pancreas of the KC-genotype mice with *P. gingivalis* applied in their oral cavities and then administrated with the probiotic composition, BPC represented benign pancreas cells, PanIns represented pancreas intraepithelial neoplasia, and AC represented adenocarcinoma cells.

As shown by results in FIGS. 2A and 2B, after the KC-genotype mice were applied with *P. gingivalis* in their oral cavities to induce pancreatic cancer, many cancer areas occurred in the pancreas tissues, as shown in FIG. 2B.

However, as shown by the result in FIG. 2C, when the KC-genotype mice were applied with *P. gingivalis* in their oral cavities and then administrated with the probiotic composition, no adenocarcinoma cell (AC) generated ever, indicating that the probiotic composition consisting of *Lactobacillus paracasei* GMNL-133 and *Lactobacillus reuteri* GMNL-89 could indeed significantly improve or mitigate the neoplasia of pancreatic cancer.

3. Assessment of Effect of Probiotic Composition Inhibiting Pancreas Cell Hyperplasia Referring to FIGS. 3A to 3C, these figures showed immunohistostaining section diagrams of pancreatic proliferating cell nuclear antigen (PCNA) of the mice suffering from pancreatic cancer after the administration of the probiotic composition in accordance with one embodiment of the present invention, in which FIG. 3A represented a immunohistostaining section diagram of pancreatic PCNA of the untreated KC-genotype mouse, FIG. 3B represented a immunohistostaining section diagram of pancreatic PCNA of the KC-genotype mouse applied with *P. gingivalis* in their oral cavities, FIG. 3C represented a immunohistostaining section diagram of pancreatic PCNA of the KC-genotype mouse applied with *P. gingivalis* in their oral cavities and administrated with the probiotic composition.

As shown by results in FIGS. 3A to 3B, after the KC-genotype mice were applied with *P. gingivalis* in their oral cavities to induce pancreatic cancer, a large amount of PCNA occurs in pancreas tissues, representing a great pancreas cell hyperplasia, as shown in FIG. 3B.

However, as shown by results in FIG. 3B, when the KC-genotype mice were applied with *P. gingivalis* in their oral cavities and administrated with the probiotic composition, the pancreas cell hyperplasia marker PCNA would be significantly reduced, proving that the probiotic composition consisting of *Lactobacillus paracasei* GMNL-133 and *Lactobacillus reuteri* GMNL-89 could indeed improve or mitigate the pancreas cell hyperplasia of the mice suffering from pancreatic cancer.

4. Assessment of Effect of Probiotic Composition Reducing Pancreas Fibrosis

Figures 4A, 4B, 4C:
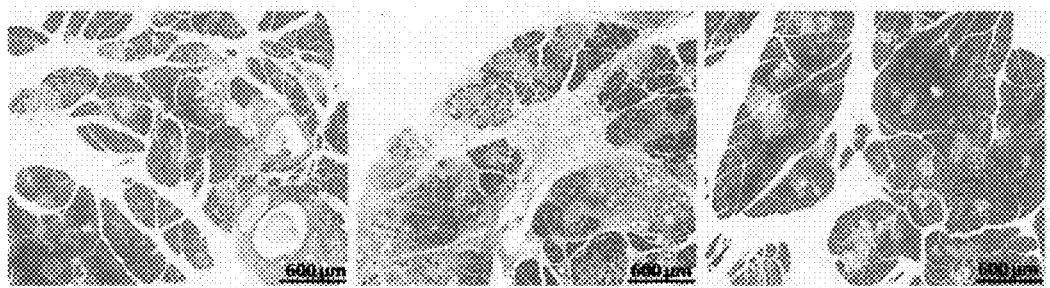
FIGS. 4A to 4F show an immunohistostaining section diagram of pancreas collagen of a mouse suffering from pancreatic cancer after the administration of the probiotic composition in accordance with one embodiment of the present invention.
Figures 4D, 4E, 4F:

Referring to FIGS. 4A to 4F, these figures showed immunohistostaining section diagrams of pancreatic collagen of mice suffering from pancreatic cancer after the administration of the probiotic composition in accordance with one embodiment of the present invention, in which FIGS. 4A to 4C corresponded to FIGS. 4D to 4F in sequence, except that the scale in FIGS. 4A to 4C was 600 μm while the scale in FIGS. 4D to 4F was 150 μm. FIGS. 4A and 4D represented immunohistostaining section diagrams of pancreatic collagen of untreated KC-genotype mice, FIGS. 4B and 4E represented immunohistostaining section diagrams of pancreatic collagen of the KC-genotype mice applied with *P. gingivalis* in their oral cavities, and FIGS. 4C and 4F represented immunohistostaining section diagrams of pancreatic collagen of the KC-genotype mice applied with *P. gingivalis* in their oral cavities and administrated with the probiotic composition.

It was shown by results in FIGS. 4A, 4B, 4D and 4E that after the KC-genotype mice were applied with *P. gingivalis* in their oral cavities to induce pancreatic cancer, a large amount of collagen occurred in pancreas tissues, representing pancreas fibrosis, as shown in FIGS. 4B and 4E.

However, as shown by results in FIGS. 4C and 4F, when the KC-genotype mice were applied with *P. gingivalis* in their oral cavities and administrated with the probiotic composition, the expression level of pancreas collagen was significantly reduced, proving that the probiotic composition consisting of *Lactobacillus paracasei* GMNL-133 and *Lactobacillus reuteri* GMNL-89 could indeed improve or mitigate the pancreas fibrosis severity of the mice suffering from pancreatic cancer.

5. Assessment of Effect of Probiotic Composition Inhibiting Expression Level of Cancer Metastasis Indicator Protein Referring to FIGS. 5A to 5L, these figures showed immunohistostaining section diagrams of N-Cad (FIGS. 5A to 5C), vimentin (FIGS. 5D to 5F), Snail-1 (FIGS. 5G to 5I) and ZEB (FIGS. 5J to 5L) of the pancreas of the mice suffering from pancreatic cancer after the administration of the probiotic composition according to one embodiment of the present invention. FIGS. 5A, 5D, 5G, and 5J represented immunohistostaining section diagrams of pancreas of untreated KC-genotype mice, FIGS. 5B, 5E, 5H, and 5K represented pancreas immunohistostaining section diagrams of the KC-genotype mice applied with *P. gingivalis* in their oral cavities, and FIGS. 5C, 5F, 5I, and 5L represented immunohistostaining section diagrams of pancreas of the KC-genotype mice applied with *P. gingivalis* in their oral cavities and then administrated with the probiotic composition.

Figure 5A:
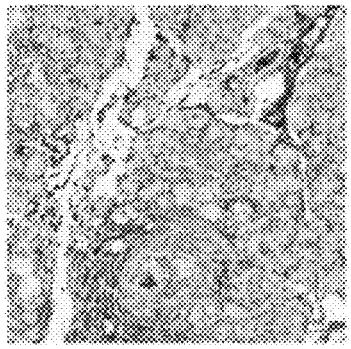
FIGS. 5A to 5L show an immunohistostaining section diagram of pancreas N-Cad (FIGS. 5A to 5C), vimentin (FIGS. 5D to 5F), Snail-1 (FIGS. 5G to 5I), and ZEB (FIGS. 5J to 5L) of a mouse suffering from pancreatic cancer after the administration of the probiotic composition in accordance with one embodiment of the present invention.
Figure 5B:
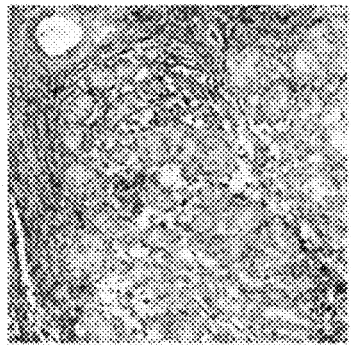
Figure 5C:
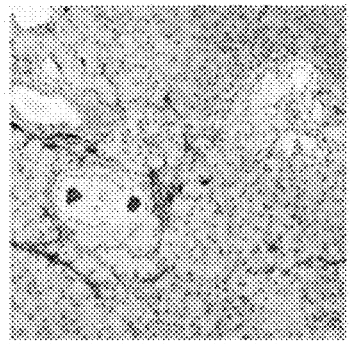
Figure 5D:
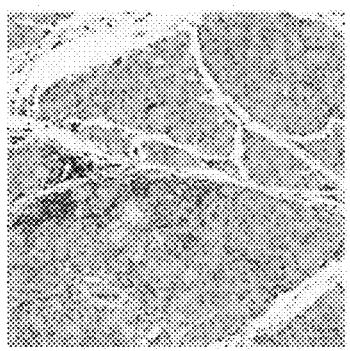
Figure 5E:
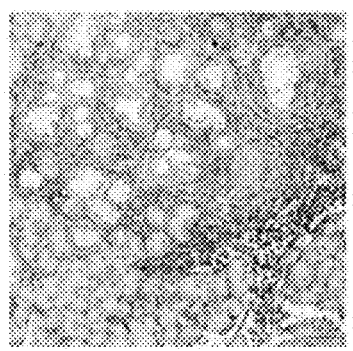
Figure 5F:
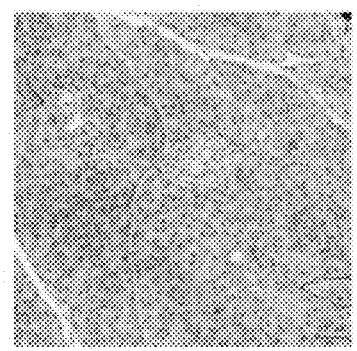
Figure 5G:
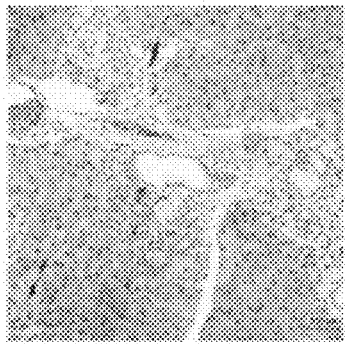
Figure 5H:
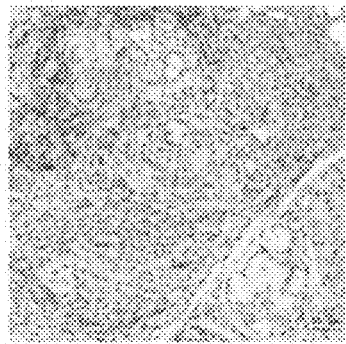
Figure 5I:
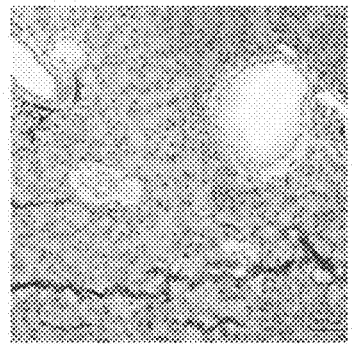
Figure 5J:
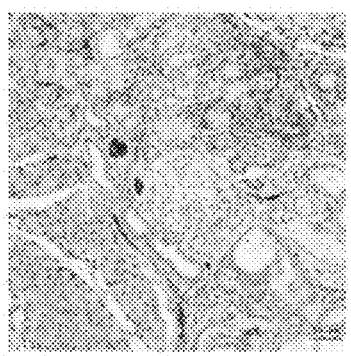
Figure 5K:
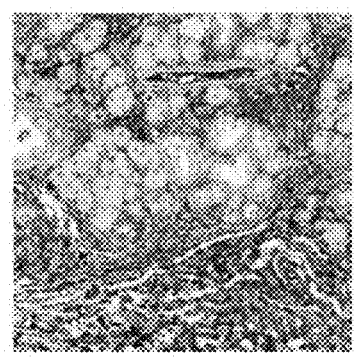
Figure 5L:
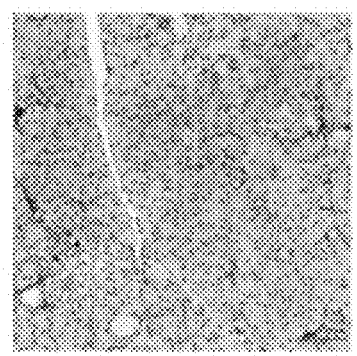

It was shown by results in FIGS. 5A, 5B, 5D, and 5E that after the KC-genotype mice were applied with *P. gingivalis* in their oral cavities to induce pancreatic cancer, a high expression level of mesenchymal markers such as N-Cad and vimentin occurred in pancreas tissues, as shown in FIGS. 5B and 5E, representing that the pancreatic cancer cell has turned into a morphology easier to transfer. Next, as shown by results in FIGS. 5G, 5H, 5J, and 5K, a high expression level of proteins facilitating the cancer metastasis, such as Snail-1 and ZEB, occurred in pancreas tissues, as shown in FIGS. 5H and 5K, representing the pancreatic cancer cell had turned into a malignant morphology easier to transfer.

However, as shown by results in FIGS. 5C, 5F, 5I, and 5L, when the KC-genotype mice were applied with *P. gingivalis* in their oral cavities and administrated with the probiotic composition, the expression levels of N-Cad, vimentin, Snail-1 and ZEB of pancreas were significantly reduced, proving that the probiotic composition consisting of *Lactobacillus paracasei* GMNL-133 and *Lactobacillus reuteri* GMNL-89 could indeed improve or mitigate the severity of pancreatic cancer tumorigenesis.

Example 4. Assessment of Effect of Probiotic Composition Modulating TGF-β-Related Signaling Pathways to Improve or Mitigate Severity of Pancreatic Cancer In the progress of the pancreatic cancer, cytokines for adjusting and controlling the immunity system were also very important, in which the TGF-β and its upstream and downstream signaling pathways could be the potential key to promote the severity of pancreatic cancer.

Referring to FIGS. 6A to 6F, they showed immunohistostaining section diagrams of the pancreatic transforming growth factor (TGF)-β (FIGS. 6A to 6C) and phospho-Smad3 (FIGS. 6D to 6F) protein of the mice suffering from pancreatic cancer after the administration of the probiotic composition in accordance with one embodiment of the present invention, FIGS. 6A and 6D represented untreated KC-genotype mice, FIGS. 6B and 6E represented immunohistostaining section diagrams of pancreas of the KC-genotype mice applied with *P. gingivalis* in their oral cavities, FIGS. 6C and 6F represented immunohistostaining section diagrams of pancreas of the KC-genotype mice applied with *P. gingivalis* in their oral cavities and administrated with the probiotic composition.

It was shown by results in FIGS. 6A, 6B, 6D, and 6E that after the KC-genotype mice were applied with *P. gingivalis* in their oral cavities to induce pancreatic cancer, a high expression level of TGF-β (as shown in FIG. 6B) occurred in pancreas tissues and thus activate (phosphorylate) its downstream Smad3 protein (as shown in FIG. 6E).

However, as shown by results in FIGS. 6C and 6F, when the KC-genotype mice were applied with *P. gingivalis* in their oral cavities and administrated with the probiotic composition, the expression level of the TGF-β (as shown in FIG. 6C) and its downstream phosphorylated Smad3 protein (as shown in FIG. 6F) in the pancreas tissues was obviously reduced, proving that the probiotic composition consisting of *Lactobacillus paracasei* GMNL-133 and *Lactobacillus reuteri* GMNL-89 could improve or mitigate the severity of pancreatic cancer through the TGF-β-related signaling pathways.

As shown in the above mentioned results, the LSL-Kras$^{G12D}$ transgenic mice were used as the animal model in the present invention, for which the pancreatic cancer was induced by using *P. gingivalis*, various conditions related to pancreatic cancer (symptomatic indicators thereof could be, for example, the pancreas weight increment, pancreas tissue tumorigenesis, and over hyperplasia) occur, and the severity of pancreatic cancer (the severity could be, for example, increased pancreas fibrosis, increased pancreatic cancer metastasis markers) was deteriorated. The aforementioned pancreas over-fibrosis could relatively inhibit the treatment effect of anti-cancer drugs, while the pancreatic cancer metastasis was the main factor causing the high severity of pancreatic cancer. However, when administrating the probiotic composition in the present invention, which was consisted of *Lactobacillus paracasei* GMNL-133 and/or *Lactobacillus reuteri* GMNL-89, the symptomatic indicators and severity of the aforementioned pancreatic cancer could be significantly improved or alleviated.

The present invention also proved that the probiotic composition consisted of the *Lactobacillus paracasei* GMNL-133 and the *Lactobacillus reuteri* GMNL-89 could inhibit the downstream phosphorylated Smad protein signaling of the pancreas through modulating TGF-β expression level of the pancreas, thus achieving the immunity adjustment effect and even mitigating the pancreatic cancer progress and severity. Moreover, since the *Lactobacillus paracasei* GMNL-133 and/or *Lactobacillus reuteri* GMNL-89 were originally isolated from the human intestinal tracts, they were safe without side effect so that they indeed had the potential to be applied in the oral composition for preventing and treating the pancreatic cancer.

It should be supplemented that, although there were some research results showing that some *lactobacillus* could inhibit the periodontal disease by inhibiting the growth of *P. gingivalis*, according to the experimental results of early stages, the probiotic composition of the present invention had no significantly bacteriostatic ability against *P. gingivalis* (not shown in the figures). Therefore, it excludes the possibility that the probiotic composition of the present invention could directly inhibit the *P. gingivalis* growth for improving pancreatic cancer symptoms.

In summary, although the probiotic composition for preventing, improving or alleviating the pancreatic cancer and a method for preventing, improving or alleviating the pancreatic cancer and its complications using the probiotic composition are illustrated by using specific combinations and specific ratios of the strains, specific routes of administration, or specific methods of evaluations as examples in the present invention, any one of ordinary skills in the art of the present invention can realize that the present invention was not limited thereto, and the present invention can also be implemented by using other combinations or other ratios of the strains, other routes of administration or other methods of evaluations without departing from the spirit and scope of the present invention.

The probiotic composition for preventing, improving or alleviating the pancreatic cancer and the method for preventing, improving or alleviating the pancreatic cancer and its complications using the probiotic composition of the present invention can be understood from the aforementioned Examples, which has the advantages that the probiotic composition is consisted of specific strains and specific ratios of *Lactobacillus paracasei* to *Lactobacillus reuteri* and thus can significantly improve or alleviate various symptomatic indicators and severity of the pancreatic cancer, thereby enabling its application of the use for preparing an oral composition for preventing, improving or alleviating the pancreatic cancer.

Although the present invention has been disclosed in several embodiments as mentioned above, these embodiments do not intend to limit the present invention. Various changes and modifications can be made by any one of ordinary skills in the art to which the present invention pertains, without departing from the spirit and scope of the present invention. Therefore, the claimed scope of the present invention shall be defined by the appended claims.

What is claimed is:

1. A method for alleviating the pancreatic cancer using a probiotic composition, comprising orally administrating the probiotic composition to an subject with an effective dose per day of 8.2×10$^8$ colony forming units (CFUs) per kg of body weight for 4 weeks, so as to reduce a symptomatic indicator and/or an indicator protein of the pancreatic cancer of the subject, wherein the probiotic composition comprises: *Lactobacillus paracasei* GMNL-133, wherein the *Lactobacillus paracasei* GMNL-133 is deposited with an accession number of CCTCC M 2011331 in China Center for Type Culture Collection (CCTCC), Wuhan University, Wuhan 430072, People's Republic of China, on Sep. 26, 2011; and *Lactobacillus reuteri* GMNL-89, wherein the *Lactobacillus reuteri* GMNL-89 was deposited with an accession number of CCTCC M 207154 in China Center for Type Culture Collection (CCTCC), Wuhan University, Wuhan 430072, People's Republic of China, on Nov. 19, 2007, and wherein the ratio of the *Lactobacillus paracasei* GMNL-133 to the *Lactobacillus reuteri* GMNL-89 in bacterial cell numbers is 2:1 to 1:2.

2. The method for alleviating the pancreatic cancer using the probiotic composition of claim 1, wherein the symptomatic indicator is selected from a group consisting of a pancreas weight, pancreas intraepithelial neoplasia, and a pancreas collagen expression level.

3. The method for alleviating the pancreatic cancer using the probiotic composition of claim 1, wherein the indicator protein comprises a cancer metastasis indicator protein.

4. The method for alleviating the pancreatic cancer using the probiotic composition of claim 3, wherein the cancer metastasis indicator protein is selected from a group consisted of the proliferating cell nuclear antigen (PCNA), N-cadherin (N-Cad), vimentin, a transcription factor Snail-1 and a zinc finger E-box binding homeobox (ZEB) protein.

5. The method alleviating the pancreatic cancer using the probiotic composition of claim 1, wherein the indicator protein comprises a transforming growth factor (TGF)-β and/or a phosphorylated Smad3 (phospho-Smad3) protein.

6. The method for alleviating the pancreatic cancer using the probiotic composition of claim 1, wherein the ratio of the

*Lactobacillus paracasei* GMNL-133 to the *Lactobacillus reuteri* GMNL-89 in the bacterial cells is 1:1.

* * * * *

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial sequence
<220> FEATURE:
<223> OTHER INFORMATION: forward primer (PAF)

<400> SEQUENCE: 1
agagtttgat cctggctcag                                              20

<210> SEQ ID NO 2
<211> LENGTH: 18
<212> TYPE: DNA
<213> ORGANISM: Artificial sequence
<220> FEATURE:
<223> OTHER INFORMATION: reverse primer (536R)

<400> SEQUENCE: 2
gtattaccgc ggctgctg                                                18

<210> SEQ ID NO 3
<211> LENGTH: 521
<212> TYPE: DNA
```

```
<213> ORGANISM: Artificial sequence
<220> FEATURE:
<223> OTHER INFORMATION: 16S rDNA partial sequence of Lactobacillus
      paracasei

<400> SEQUENCE: 3
tctgcggtgc ctatacatgc aagtcgtacg cactggccca actgattgat ggtgcttgca        60
cctgattgac gatggatcac cagtgagtgg cggacgggtg agtaacacgt aggtaacctg       120
ccccggagcg ggggataaca tttggaaaca gatgctaata ccgcataaca acaaaagcca       180
catggctttt gtttgaaaga tggctttggc tatcactctg ggatggacct gcggtgcatt       240
agctagttgg taaggtaacg gcttaccaag gcgatgatgc atagccgagt tgagagactg       300
atcggccaca atggaactga gacacggtcc atactcctac gggaggcagc agtagggaat       360
cttccacaat gggcgcaagc ctgatggagc aacaccgcgt gagtgaagaa gggtttcggc       420
tcgtaaagct ctgttgttgg agaagaacgt gcgtgagagt aactgttcac gcagtgacgg       480
tatccaacca gaaagtcacg gctaactacg tgccagatgg g                          521

<210> SEQ ID NO 4
<211> LENGTH: 521
<212> TYPE: DNA
<213> ORGANISM: Artificial sequence
<220> FEATURE:
<223> OTHER INFORMATION: 16S rDNA partial sequence of Lactobacillus
      reuteri

<400> SEQUENCE: 4
tctgcggtgc ctatacatgc aagtcgtacg cactggccca actgattgat ggtgcttgca        60
cctgattgac gatggatcac cagtgagtgg cggacgggtg agtaacacgt aggtaacctg       120
ccccggagcg ggggataaca tttggaaaca gatgctaata ccgcataaca acaaaagcca       180
catggctttt gtttgaaaga tggctttggc tatcactctg ggatggacct gcggtgcatt       240
agctagttgg taaggtaacg gcttaccaag gcgatgatgc atagccgagt tgagagactg       300
atcggccaca atggaactga gacacggtcc atactcctac gggaggcagc agtagggaat       360
cttccacaat gggcgcaagc ctgatggagc aacaccgcgt gagtgaagaa gggtttcggc       420
tcgtaaagct ctgttgttgg agaagaacgt gcgtgagagt aactgttcac gcagtgacgg       480
tatccaacca gaaagtcacg gctaactacg tgccagatgg g                          521
```